United States Patent [19]
Homsy

[11] Patent Number: 5,176,712
[45] Date of Patent: Jan. 5, 1993

[54] ENDOPROSTHESES WITH RESORPTION PREVENTING MEANS

[75] Inventor: Charles A. Homsy, Houston, Tex.

[73] Assignee: Tranquil Prospects Ltd., Tortola, British Virgin Isls.

[21] Appl. No.: 180,467

[22] Filed: Apr. 12, 1988

[51] Int. Cl.⁵ .............................................. A61F 2/32
[52] U.S. Cl. ........................................ 623/23; 623/18
[58] Field of Search ................... 623/16, 18, 19, 20, 623/21, 22, 23

[56] References Cited

U.S. PATENT DOCUMENTS 4,636,214  1/1987  Homsy .

FOREIGN PATENT DOCUMENTS 2247721  4/1974  Fed. Rep. of Germany ........ 623/22

OTHER PUBLICATIONS

Homsy, et al. "Porous Implant Syst. for Prosth. Stabilization" Clinical Orthopaedics, No. 89 Nov.-Dec. 1972 pp. 220-234.

Primary Examiner—David Isabella
Attorney, Agent, or Firm—Michael P. Breston

[57] ABSTRACT

The endoprosthesis is adapted for insertion into a socket formed within the medullary canal of a patient's bone. It comprises an elongated stem defining a proximal region, a distal region, and a tip. A soft porous pad extends distally from the stem tip. The pad has a thickness greater than two millimeters. The distal region is preferably biocompatible, porous, soft, resilient, deformable, and tissue-ingrowth promoting.

12 Claims, 3 Drawing Sheets

ENDOPROSTHESES WITH RESORPTION PREVENTING MEANS

This application is related to patent application Ser. No. 07/180,466, filed on even date and now U.S. Pat. No. 5,002,488, issued Mar. 26, 1991.

BACKGROUND OF THE INVENTION

1. Field of the Invention

The invention relates to endoprostheses of the type which include a stem for insertion into a canal of a bone, such as a medullary canal of a femur.

2. Description of the Prior Art

Endoprostheses include implants which rely on an accurate press-fit to become established between an uncoated stem and the surrounding bone of the femur, implants which rely on tissue ingrowth into a porous soft coating which covers the entire stem, and implants which rely in part on a postoperative biological bond to become established between the surrounding bone and a hard surface porosity on the proximal stem.

Initially, these hard surface porosities were porous coatings bonded to the entire surface of the stem. It was found that bone would bond to the apposite hard porous coating. While such bonding was desired for the proximal stem, it was very detrimental to the distal femur, as subsequently explained.

In an effort to prevent this distal bond, in recent hip joint endoprostheses, the hard surface porosity is confined mostly to the proximal stem, and the distal stem surface is purposely left bare.

Unfortunately, clinical evidence has shown that the various attempts, at using hard porosities for achieving long-lasting, adequate proximal load transfer and proximal implant stability and fixation, have not been entirely satisfactory because a thin bone phase forms externally on the distal femur, and a dense and thick bone forms under the stem tip within the medullary canal.

Such a dense and thick bone under the stem tip will increasingly shunt the load from the proximal femur to the distal femur in the region apposite to the stem tip, and will lead to proximal bone resorption. Femoral bone resorption reduces the proximal femur's resistance to implant rotation and further accelerates the bone resorption process, which is unavoidably accompanied by implant instability, great discomfort, and severe pain.

Even an endoprosthesis having a soft, tissue-promoting coating over its entire stem surface has been found also to experience thin bone growth around the stem tip.

It is an object of this invention to provide different types of endoprostheses with bone resorption preventing means that alleviate the load shunting problem.

SUMMARY OF THE INVENTION

The relatively intense axial and rotational cyclic strain and stresses which would be transmitted by the distal tip of the stem to the apposite bone are relieved in accordance with this invention by an extension which is added to the tip of the distal stem. This extension substantially eliminates or attenuates the transfer of these stresses by the distal stem to the apposite cortical bone of the femur in the diaphyseal region.

The endoprosthesis is adapted for insertion into a socket formed within the medullary canal of a patient's bone. It comprises an elongated stem defining a proximal surface, a distal surface, and a tip. A soft porous pad extends distally from the stem tip. The pad has a thickness greater than two millimeters. The distal surface is preferably biocompatible, porous, soft, resilient, deformable, and tissue-ingrowth promoting.

In another embodiment, the stem surface is substantially entirely biocompatible, porous, soft, resilient, deformable, and tissue-ingrowth promoting.

In a further embodiment, at least a portion of the proximal surface is biocompatible, porous, deformable, and tissue-ingrowth promoting, and another portion of the proximal surface is biocompatible, porous, nondeformable, and tissue-ingrowth promoting.

DETAILED DESCRIPTION OF PREFERRED EMBODIMENTS

Figure 6:
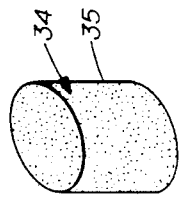
FIG. 6 is a perspective view of the pad shown in FIG. 5.

While the invention will be illustrated for reconstructing the long bone or femur of a hip joint, it is not limited thereto and can be used with endoprostheses for other body joints.

The same numerals will be used to designate the same or similar parts, whenever possible, to simplify the drawings.

A brief description of a prior art hip joint, medullary endoprosthesis implant 10, within a preformed socket within a femur, will facilitate the understanding of the problems solved by the invention.

Implant 10 (FIGS. 1-4) includes a neck 11 and a stem 12 which has a proximal exterior or outside region 13, a distal exterior or outside region 14, and a distal tip 15. As used herein in respect to stem 12, the word "region" may be a three-dimensional locus of points which has depth. For example, distal stem region 14 can be a layer, or a coating, or the exterior surface of stem 12.

If accurately fitted, stem 12 can transfer appropriate stresses to the femur 16, which has a proximal region 17 and a distal region 18. The accuracy of fit, however, is in practice very difficult to achieve. Therefore, some stems 12 are additionally provided with collars 19 to help them transmit load to the superior surface 20 of the cut femoral neck.

The medullary canal in proximal femur 17 has a complex sectional shape whose major axis is in the medial-lateral direction. Then the canal's sectional shape gradually changes to increasingly circular in the diaphyseal region of distal femur 18.

More distally, the near circular sectional shape can again change to the complex shape but this time with its major axis in the anterior/posterior direction.

Figure 4:
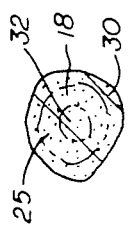
FIG. 4 is a sectional view taken on line 4—4 of FIG. 3.

The surgeon forms, within the medullary canal, a socket 21, which has a proximal region 22 and a distal region 23. Socket 21 is defined by hard cancellous bone 24 (FIG. 14) and by dense compact cortical bone 25 in the epiphyseal and metaphyseal regions, following the removal of the softer cancellous bone from within these regions. In the diaphyseal region, socket 21 is defined only by cortical bone 25 (FIG. 4).

In an attempt to avoid intruding into viable bone, stem 12 is shaped to seat centrally in and follow the natural contours of socket 21.

To mimic the contour and shape of proximal stem 13 (FIG. 13), the sectional shape of proximal socket 22 is generally trapezoidal, but with rounded corners, whose major axis is in the medial/lateral direction and, in distal socket 23 (FIG. 1), the sectional shape gradually changes to increasingly circular but of reduced area.

For use with the uncoated implant 10 without cement or grout, the surgeon generally shapes socket 21 to conform as closely as possible to the geometrical shape of its stem 12. He intends to obtain, intraoperatively, a generally uniform press fit between stem 12 and the appositional hard cancellous and cortical bones 24,25, respectively.

If a perfect press-fit is achieved, the prepared socket 21 has, at each point over substantially its entire length, a transverse sectional area which corresponds substantially with the corresponding transverse sectional area of stem 12 at that point.

An implant 10 which combines a uniform press-fit between proximal stem 13 and the appositional hard cancellous bone 24, and which, in addition, has a collar 19 that is shaped to precisely match the apposite cut surface 20 on the femoral neck, can transfer loads to proximal femur 17 so as to develop strains therein that are similar to those induced by normal hip joint movements within an intact femur. In practice, however, such a press-fit and perfect collar match are very difficult to achieve intraoperatively.

In use, the resistance to stem rotation is in large part the result of keying the sectional shape of proximal stem 13 (FIG. 14) to a corresponding sectional shape of proximal socket 22.

In response to hip joint loads produced by normal ambulation, proximal stem 13 distributes stresses to proximal femur 17, circumferentially, in the form of tensile hoop stresses, and longitudinally in the form of compressive medial stresses and of tensile lateral stresses.

Distal stem 14 (FIGS. 1-4) and/or its stem tip 15 transfer corresponding stresses and strains to the apposite cortical bone 25 in the distal femur 18. Distal femur 18 may respond to the received stresses by enlarging its bone structure, which can manifest itself as an external boss 30 on distal femur 18, and as an internal bridge 32 under stem tip 15.

Such bone formation is believed to be prompted by relatively intense stresses which are transmitted, at least in part, through stem tip 15 to the apposite bone. Such stresses are believed to be caused by axial bending and torsional cyclic forces acting about the long axis of stem 12 in response to normal hip joint ambulation.

Figure 2:
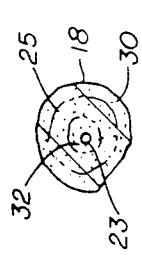
FIG. 2 is a sectional view taken on line 2—2 of FIG. 1.
Figure 3:
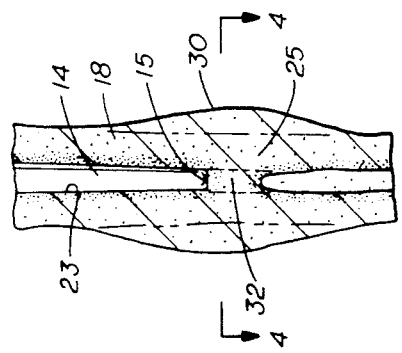
FIG. 3 is an enlarged elevational view of the distal femur of FIG. 1, showing the socket under the stem tip to be totally plugged up, and showing the external bone growth on the distal femur.
Figure 1:
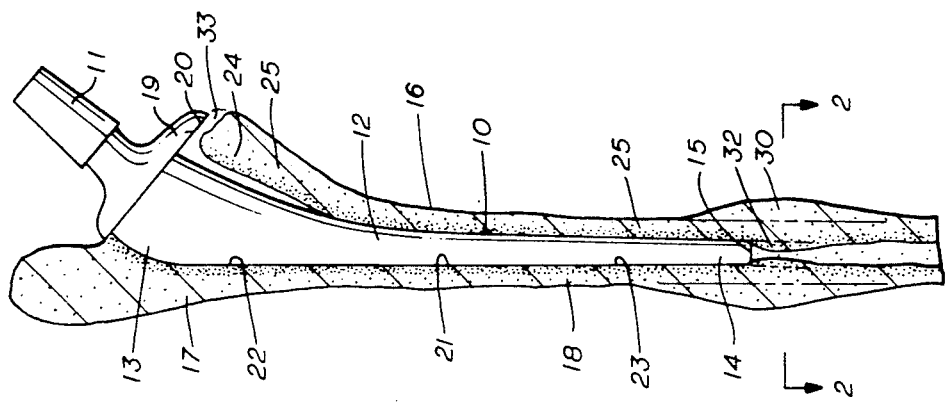
FIG. 1 is an elevational view of a known uncoated hip endoprosthesis shown within a femur, in which the distal stem socket under the stem tip is nearly totally plugged up by inward bone growth, and in which the bone resorption process has already well progressed.
Figure 9:
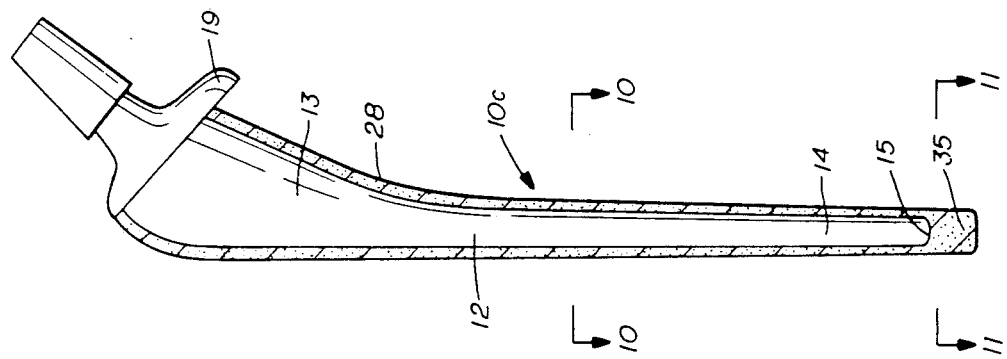
FIG. 9 is an elevational view of a known endoprosthesis whose stem is coated with a very soft porous layer, shown in section, and which utilizes the pad below its stem tip.
Figure 8:
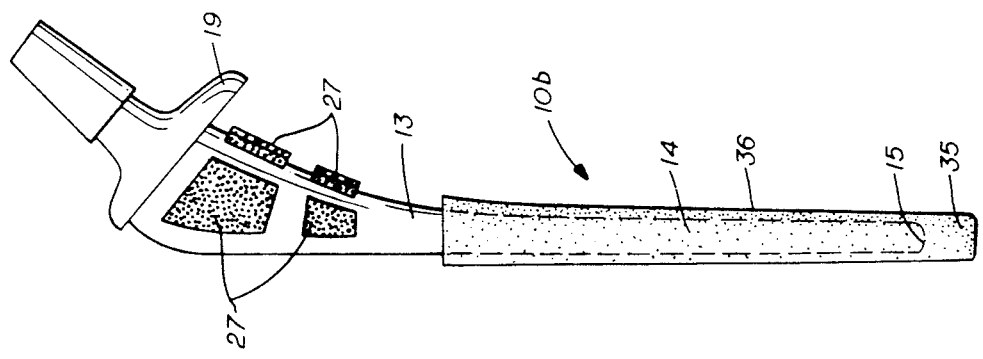
FIG. 8 is an elevational view of a known endoprosthesis coated with discrete porous metal patches on the surface of its proximal stem and which utilizes the pad shown in FIG. 6 and the sleeve shown in FIG. 7.
Figure 7:
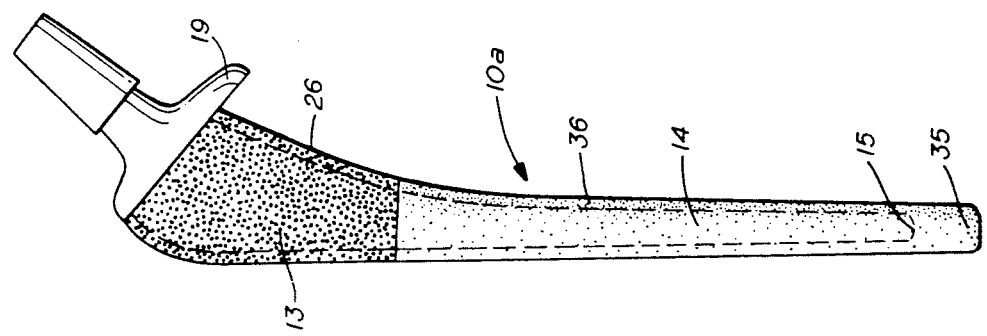
FIG. 7 is an elevational view of a known endoprosthesis that is fully coated with porous metal on the surface of its proximal stem, and which is shown together with an improved embodiment of the invention, which includes the pad of FIG. 6 and also a soft, porous, biocompatible distal sleeve or coating extending upwardly from the pad on the bare surface of the stem.
Figure 12:
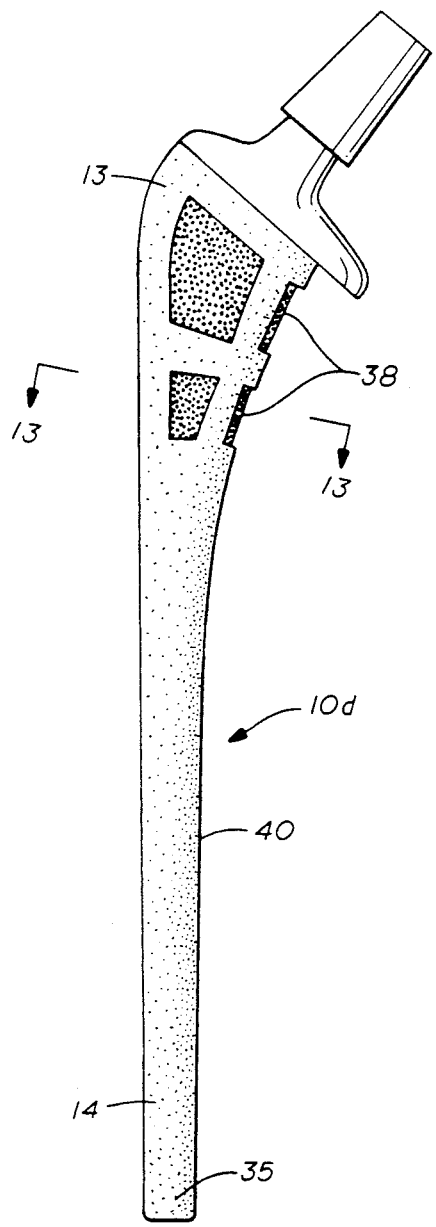
FIG. 12 is an elevational view of a novel endoprosthesis coated with discrete porous metal patches on the surface of its proximal stem; it also has a soft, porous, biocompatible sleeve or coating over the entire bare surface of the stem, and utilizes the pad below the stem tip.

In FIGS. 1 and 2, bridge 32 is shown as being nearly fully developed. When it is already fully formed (FIGS. 3-4), it effectively plugs up distal socket 23 below stem tip 15, and it has the necessary strength to fully react against the physiological ambulation loads transmitted to and/or through stem tip 15.

The more reaction forces that are provided by more or less formed bridge 32, the less reaction forces will be needed from proximal femur 17. This principle is known as "load shunting" from proximal femur 17 to distal femur 18.

It is believed that the transfer by distal stem 14, and/or its stem tip 15, of stresses and strains to the apposite cortical bone 25 in the distal femur 18, and the consequential formation of bridge 32, are the primary causes for the proximal, gradual, osseous resorption, generally designated as 33 (FIG. 1), which takes place within proximal femur 17, especially on its anterior, posterior and medial aspects.

As the decalcification or osseous resorption 33 increases, proximal femur 17 becomes less and less able to resist the dangerous and increasing tendency of proximal stem 13 to rotate within proximal socket 22, as well as the tendency by stem tip 15 to toggle. All of which further prompts femur 16 to stimulate osseous production under stem tip 15, which further accelerates the proximal osseous resorption already in progress until, sooner or later, a sufficient loosening of stem 12 within its socket 21 takes place, which is accompanied by great pain and extraordinary discomfort to the patient.

In order to eliminate or substantially reduce the femur's resorption, there is provided, in accordance with this invention, an energy absorbing means 34 which is designed to substantially absorb the mechanical energy that is being transferred to and/or through distal stem 14 and/or its tip 15, or at least to largely attenuate the intensity of such loads that do transfer, to the apposite cortical bone 25 in the diaphyseal region 18 of femur 16.

The present invention has utility for uncoated endoprostheses and for those endoprostheses whose stems receive hard surface porosities, as will now be illustrated.

Figure 5:
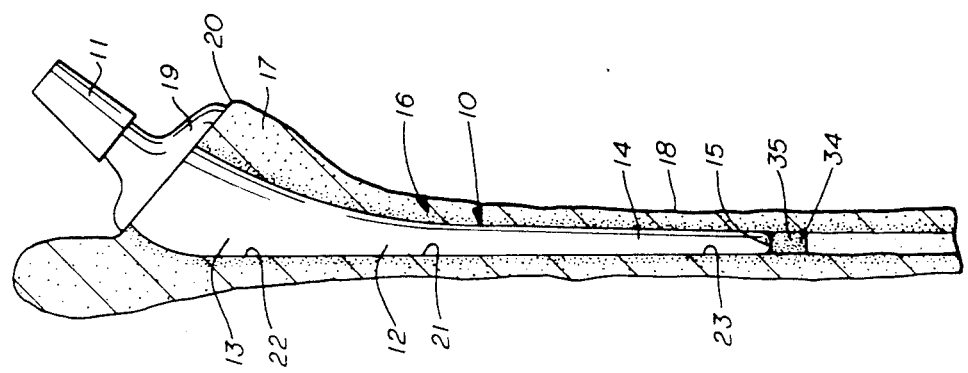
FIG. 5 is an elevational view of the uncoated endoprosthesis of FIG. 1 together with a simple embodiment of the invention, which includes a soft, porous, biocompatible pad.

Implant 10 (FIGS. 1-6) has an uncoated stem 12 which is associated, in accordance with this invention, with a simple embodiment of the energy absorbing means 34. This embodiment is a pad 35. Pad 35 may be disposed adjacent and opposite to stem tip 15 (FIG. 5), or preferably it is bonded to stem tip 15 (FIGS. 6-9, 11-12).

Implant 10a (FIG. 7) has a proximal stem region 13 which is coated with a continuous thin, hard porous coating 26. In accordance with this invention, the energy absorbing means 34, in addition to pad 35, also includes a soft, porous, distal sleeve or coating 36 extending upwardly from and being continuous with pad 35. Coating 36 is applied to the bare metal of stem 12 in a suitable manner to fix it securely thereto. Soft sleeve 36 is confined mainly to the distal stem region 14.

Pad 35 and coating 36 serve to absorb or largely attenuate the longitudinal, lateral, and rotational stresses and micromotions transferred to distal stem 14.

Such energy absorption or attenuation in the region appositional to distal stem tip 15 prevents unnatural load shunting to distal femur 18 and, more importantly, reduces localized stress zones therein, thereby fostering favorable conditions for long-term fixation of proximal stem 13, maintaining its load transfer capabilities, and ensuring the osseous integrity of proximal femur 17.

Implant 10b (FIG. 8) has a proximal stem region 13, which is coated with discrete hard porous patches 27, and a distal stem region 14, which receives pad 35 and sleeve 36.

Implants 10a and 10b are implanted without the use of cement or grout. It is intended that when proximal stem 13 is inserted into proximal socket 22, a press-fit will form at least between the hard coatings and the apposite hard cancellous bone 24. To allow for a press-fit of soft coating 36, socket 21 is made to have, at each point adjacent to the soft coating 36, a transverse sectional area which is slightly less than the corresponding transverse sectional area of soft coated stem 12 at that point.

At the junction between hard and soft coatings on the stem of implant 10a, the soft coated cross-sections will be larger than adjacent hard-coated cross-sections, so that following compression of the soft coating, the hard coating will have a press-fit against adjacent hard cancellous bone 24 and/or cortical bone 25.

Figure 10:
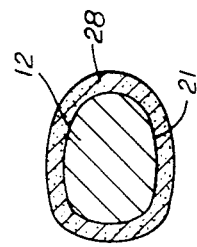
FIG. 10 is a sectional view on line 10—10 of FIG. 9.
Figure 11:
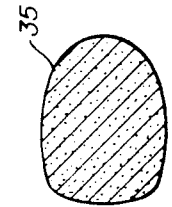
FIG. 11 is a sectional view on line 11—11 of FIG. 9.

Implant 10c (FIGS. 9-11) has a stem 12 which is substantially fully coated with a very soft, tissue-ingrowth promoting, very porous coating 28 over its entire bare outer surface. The distal stem region 14 of implant 10c receives pad 35 below stem tip 15.

Implant 10c is more fully described in U.S. Pat. No. 4,636,214 and in copending application 815,394 filed Dec. 31, 1985. Implant 10c is also briefly described in a brochure of Vitek, Inc., dated 1986 and titled ANAFORM Femoral Endoprosthesis System. ANAFORM is a trademark of Vitek Inc.

Implant 10d (FIGS. 12-14) has discrete, hard porous patches 38 on the proximal stem region 13. The entire remainder of the bare outer surface of stem 12 is coated with a soft, porous coating 40. Distal stem region 14 also receives pad 35 below stem tip 15.

To use implants 10c and 10d, the surgeon shapes socket 21 to conform as perfectly as possible to the geometric shape of stem 12. To allow for the compression of soft coating 28 or soft coating 40, socket 21 is made to have, at each point over substantially its entire length, a transverse sectional area which is slightly less than the corresponding transverse sectional area of coated stem 12 at that point.

Figure 13:
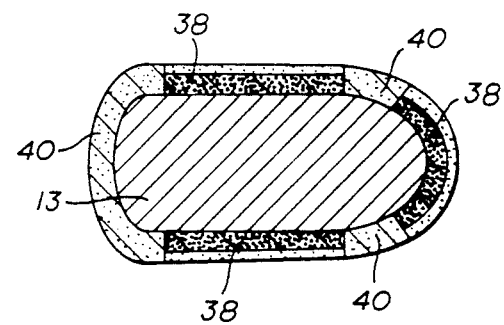
FIG. 13 is a sectional view taken on line 13—13 of FIG. 12.
Figure 14:
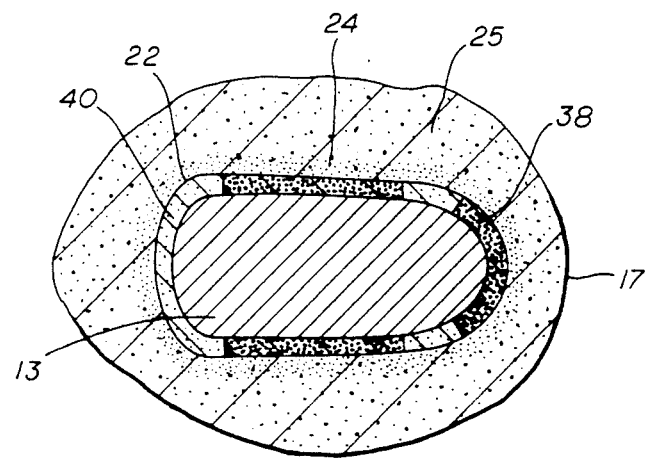
FIG. 14 is a sectional view similar to FIG. 13 but showing the stem within its socket in the femur.

The soft porous coating must compress at least by a sufficient amount so as to reduce the overall dimension of the coated stem to that of the porous metal (compare FIGS. 13 and 14).

When coated stem 12 is forcefully inserted into socket 21, each soft porous coating 28, 36 or 40 becomes compressed (FIG. 13) and provides a desired press-fit, thereby achieving an optimal initial stability and an extensive surface contact area between the compressed porous coating and the appositional hard cancellous and cortical bones 24, 25, respectively.

A compression of the soft coating by about 1 to 40% will bring the hard porous metal coating into apposition with adjacent bone to maximize the possibility of bone ingrowth into the porous metal. At the same time such biological bonding with the hard coating will be augmented by fibrous tissue an/or bone ingrowth into the soft deformed coating.

The compression is preferably such that at least the medial-lateral sectional shape of coated proximal stem 13 at any given point is slightly larger than the corresponding medial-lateral dimension of proximal socket 22 at that point, whereby, when stem 12 is inserted into socket 21, soft porous coating 28 or 40 becomes compressed, at least in the medial/lateral direction between the core of stem 12 and the appositional cancellous bone 24 or cortical bone 25, but without substantially restricting the porosity of coating 40.

The opportunity for tissue ingrowth into the soft and hard coatings provides an optimal initial and a long-term stability, as well as a distributed rather than a multi-point biological fixation.

If in addition, collar 19 is precisely shaped to match the appositional surface 20 of the cut femoral neck, so that postoperatively, implants 10, 10a-10d will be able to transfer loads to cut surface 20 similar to those produced by the hip joint movements in an intact femur.

The convalescing patient can immediately impose postoperatively a cyclical load on proximal femur 17. This load is analogous to the load imposed on a natural, unoperated proximal femur 17.

Implants 10 and 10a-10d are typically made of a strong, hard, biocompatible metal, such as stainless steel, cobalt-chrome, or titanium. They may also be made of a sufficiently strong composite biocompatible structure of metal with polymers, or of wholly polymeric structures, which may be reinforced with metal or ceramic or other materials, such as polyimide fiber or carbon fiber. If the implant is uncoated (FIG. 5), new bone will grow up and then interface and adapt to stem 12.

The biocompatible hard, tissue-ingrowth promoting, surface porosities 26, 27 and 38 can be ceramic, polymeric, metallic or a composite material thereof. These surface porosities can be either wholly or partially of a homogeneous porous phase, or they can be combinations of different porous phases. They can be made of porous titanium or other bicompatible metal, and said metal porosities can in turn be coated with synthetic hydroxylapatite.

A postoperative mechanical bond is formed between the living and the hard porous coated surfaces. This bond is known as biointegration. The hard porous coatings can also be designed to form a postoperative mechanical biochemical bond with the living bone. This bond is known as osseointegration.

Figure 15:
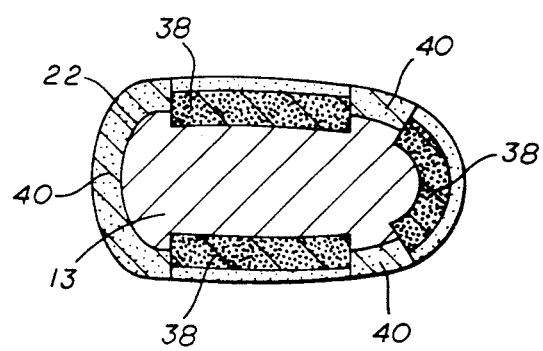
FIG. 15 is a sectional view similar to FIG. 13, but showing the porous metal coating as being recessed from the stem surface.

Hard coating 26 of implant 10a, hard patches 27 of implant 10b, and hard patches 38 of implant 10d can be on the surface of proximal stem 13 (FIG. 13), or they can be countersunk into the stem body (FIG. 15). Patches 27 on implant 10b and patches 38 on implant 10d are preferably disposed on the anterior, posterior and medial aspects of proximal stem 13.

The material out of which pad 35 and soft coatings 28, 36 and 40 are made should preferably have a three-dimensional structure characterized by at least a low-modulus of elasticity, a continuous biocompatible solid phase, and a biocompatible fluid phase.

In the preferred embodiment, the fluid phase is continuous with the ambient environment. This preferential structure should exhibit a compressive stress-strain behavior of a substantially lower order than cortical or cancellous bone. That is, it must deform under load much more readily than the appositional bone.

The material for pad 35 and the soft coatings can have an open pore size of 50 to 400 microns which has been found to be optimal. A material that meets the above criteria can be elastomeric or nonelastomeric, resilient, open or closed pore, and very soft, so that sufficient deformation in its shape can occur in response to loading by distal stem 14, as well as by any subsidence of stem 12.

This soft porous material for pad 35 should become compressed in response to an initial loading, but without substantially restricting its porosity, thereby permitting a subsequent compression to take place. Such a material will be nonstimulating to the cortical bone 25 in the distal femur region 18.

The porosity of pad 35 will allow the ingrowth therein of fibrous tissue, which will further enhance its ability to attenuate or absorb energy transferred to distal stem 14.

Pad 35 has a porosity such that its volume can shrink up to 60-80% of its original volume before substantial resistance to compression becomes manifest.

Pad 35 (FIG. 6) can be a short cylinder having an outer diameter which is slightly less than the smallest diameter of socket 21 to facilitate the insertion of stem 12 therein, or it can be slightly larger than the diameter of distal socket 23 to obtain a pressure fit with the appositional hard cortical bone 25.

Pad 35 can have a trapezoidal sectional shape with rounded corners and with the main axis in the anterior-posterior direction to better fit the corresponding shape of the distal socket 23.

It has been found that the thickness for the material from which pad 35 is made, between its interior surface apposite to the stem tip 15 and its outside surface, should be greater than 2 mm and preferably greater than 4 mm to provide adequate bio-mechanical energy absorption.

The diametrical dimension where the hard coatings are located correspond to that of the opposite proximal socket.

The soft coatings may have a variable thickness at any given cross-section of the stem so that they are thicker in the anterior-posterior direction to better fit the sectional shape of the distal socket 23.

The thickness of the resilient and deformable soft coatings may be such that the overall dimensions of the coated stem exceed the corresponding dimensions of the prepared socket 21 by an amount ranging from 0.2% to 10%.

It has been found that the thickness for the material from which the soft coatings are made should be greater than 0.5 mm and preferably greater than 1.5 mm and less than 2.5 mm.

The thickness of the soft coatings is such that they may be compressed by an amount ranging from one percent (1%) to forty percent (40%) of their original thickness without having their porosities overly reduced.

The material out of which pad 35 and soft coatings 28, 36 and 40 are made can be a porous Teflon perfluorocarbon polymer. Such materials including tissue-ingrowth promoting additives are sold by Vitek, Inc., under the trademark PROPLAST.

A PROPLAST material is a reinforced polymer which comprises polytetrafluoroethylene fibers, in admixture with a proportion of carbon or graphite fiber or particles, or aluminum oxide particles and bonded with a sintered polytetrafluoroethylene resin.

The PROPLAST materials are soft, very porous, open pore, ingrowth-promoting, compressible, and permanently deformable under very light loads.

This invention fills the need for more natural stress and strain patterns within femur 16 by optimizing the conditions for intimate engagement with appositional bone.

The present invention allows for a more stable apposition of porous metal to adjacent bone, thereby achieving an improved distributed longitudinal load transfer to femur 16. The forces per unit of surface area become largely reduced.

By immediately imposing postoperatively a cyclical load on proximal femur 17 analogous to the load of a natural, unoperated femur, proximal femur 17 responds and maintains maximal strength and resistance to stem rotation.

Thus, the surgeon can select from different endoprostheses including those which rely on an accurate press-fit to become established between an uncoated stem and the surrounding bone, and those which rely on tissue ingrowth into a porous coating on the outer stem surface.

He can choose from implants which are uncoated, coated with a very soft porous material, or coated with a hard porous material, or with a combination thereof.

What I claim is:

1. An endoprosthesis for insertion into a socket formed within the medullary canal of a patient's bone, comprising:
    an elongated stem having an outer region including: a proximal region, a distal region, and a distal tip;
    said distal tip having an energy-absorbing, biocompatible, resilient, soft, porous member having a thickness, measured in the axial direction of said stem, that is greater than two millimeters, and having a compressive stress per unit of strain which is substantially smaller than that of apposite cortical bone within said medullary canal; and
    at least a portion of said proximal region of said stem having integral therewith a biocompatible, porous and hard means which promotes tissue-ingrowth, and said hard means having a modulus of elasticity at least as great as that of cancellous bone.

2. The endoprosthesis according to claim 1, and another portion of said proximal region of said stem having integral therewith biocompatible, porous and soft means which promotes tissue-ingrowth.

3. The endoprosthesis according to claim 1, in which said proximal region of said stem having an anterior portion, and said hard means being disposed on said anterior portion.

4. The endoprosthesis according to claim 1, in which apart from said hard means, substantially the whole of the remainder of said outer region of said stem having integral therewith biocompatible, resilient, porous and soft means which promotes tissue-ingrowth.

5. The endoprosthesis according to claim 1, in which at least a portion of said distal region of said stem having integral therewith biocompatible, resilient, porous and soft means which promotes tissue-ingrowth.

6. The endoprosthesis according to claim 4, in which said porous soft means having a thickness less than 2.5 mm.

7. The endoprosthesis according to claim 5, in which said porous soft means having a thickness less than 2.5 mm.

8. The endoprosthesis according to claim 6, in which said porous soft means having a resiliency such that it can be compressed by an amount ranging from one percent (1%) to forty percent (40%) of its original thickness.

9. The endoprosthesis according to claim 7, in which said porous soft means having a resiliency such that it can be compressed by an amount ranging from one percent (1%) to forty percent (40%) of its original thickness.

10. The endoprosthesis according to claim 8, in which said porous soft means defining pores having an average effective diameter of 50 to 400 microns.

11. The endoprosthesis according to claim 9, in which said porous soft means defining pores having an average effective diameter of 50 to 400 microns.

12. The endoprosthesis according to claim 2, in which at the junction between said porous hard means and said porous soft means, the cross-section of said soft means is larger than that of said hard means so that, upon insertion of said stem into said medullary canal and following compression of said soft means, said hard means have a press-fit against apposite bone in said medullary canal.

* * * * *